United States Patent [19]
Dewaele

[11] Patent Number: 5,757,021
[45] Date of Patent: May 26, 1998

[54] IDENTIFICATION SYSTEM AND METHOD FOR USE IN THE FIELD OF DIGITAL RADIOGRAPHY

[75] Inventor: Piet Dewaele, Berchem, Belgium

[73] Assignee: Agfa-Gevaert N.V., Mortsel, Belgium

[21] Appl. No.: 593,000

[22] Filed: Jan. 29, 1996

[30] Foreign Application Priority Data

Feb. 17, 1995 [EP] European Pat. Off. ............. 95200383

[51] Int. Cl.$^6$ .................................................. G03B 42/02
[52] U.S. Cl. .......................... 250/581; 250/582; 250/584
[58] Field of Search ................................. 250/584, 581, 250/484.4, 582

[56] References Cited

U.S. PATENT DOCUMENTS 4,960,994  10/1990  Müller et al. ......................... 250/584
5,264,684  11/1993  Weil ........................................ 250/581
5,428,659  6/1995  Renner et al. ............................ 378/162

*Primary Examiner*—Edward J. Glick
*Attorney, Agent, or Firm*—Baker & Botts, L.L.P.

[57] ABSTRACT

By means of a read/write terminal patient identification data stored in a touch memory, an EEPROM, a bar code label or an RF tag are read or identification data are retrieved from a hospital identifictaion system (HIS). On the read/write terminal an examination type is selected from a displayed list of examination types. The patient identification data and the identifier of the selected examination type are associated, stored and transferred onto an RF tag provided on a cassette conveying a photostimulable phosphor screen or onto an RF tag that is attachable to the cassette. After exposure of the screen to X-rays, the RF tag and the photostimulable phosphor screen are read out and the radiation image read out of the screen is processed in accordance with processing parameters associated with the selected examination type.

33 Claims, 2 Drawing Sheets

Smith, Helen

IDENTIFICATION SYSTEM AND METHOD FOR USE IN THE FIELD OF DIGITAL RADIOGRAPHY

FIELD OF THE INVENTION

The present invention is in the field of digital radiography. The invention more specifically relates to an identification system and an identification method to be used in connection with a digital radiography system wherein a radiographic image stored in a photostimulable phosphor screen is read out and converted into an image signal.

STATE OF THE ART

In the field of digital radiography a wide variety of image acquisition techniques have been developed that render a digital representation of a radiation image.

In one of these techniques a radiation image, for example an X-ray image of an object, is stored in a screen comprising a photostimulable phosphor such as one of the phosphors described in European patent application 503 702 published on 16.09.92.

In a read out station the stored radiation image is read by line-wise scanning the screen with stimulating radiation such as laser light of the appropriate wavelength, detecting the light emitted upon stimulation and converting the emitted light into a digital signal representation that can be subjected to different kinds of image processing techniques.

The original or enhanced image can then be transmitted to a hard copy recorder for reproduction of the image on the film size and lay-out of the radiologist's choice and/or it can be applied to a monitor for display.

After read-out the residual image left on the photostimulable phosphor screen is erased so that the screen is again available for exposure.

As in conventional radiography the radiographic image needs to be associated with a patient.

Further, adjustment parameters for the components of the read out device as well as parameters to be used during image processing are to be associated with a radiographic image. Commonly the settings for the read out apparatus and the processing parameters are determined by associating with an X-ray image an identifier of the performed examination type. With this examination type a unique set of read out settings and processing parameters is linked. This set is defined and stored (in the read out apparatus) in advance.

The currently used patient and examination type identification system operates as follows.

An unexposed photostimulable phosphor screen is conveyed in a cassette that is provided with an EEPROM (Electrically Erasable Programmable Read Only Memory) having a number of electrical contacts in a fixed position an the cassette for power supply and read-write transfer of identification data.

The radiologist or operator performs a radiographic exposure of a phosphor screen in a cassette and transports the exposed cassette to an identification station.

The identification data of the patient are entered into an identification program running on the identification station. This can be performed manually by entering the data into a personal computer of the identification system.

Alternatively, in case the identification station is connected to a hospital information system (HIS) or a radiology information system (RIS), the identification data can be entered automatically. They can be retrieved via a file of known format transmitted over a computer link as has been described in European patent application 679 909.

An examination type identifier is entered manually into the identification station by selecting a specific examination type (and subtype) out of a hierarchical pop-up menu.

Then, the patient identification data and the examination type identifier are written into the EEPROM on the exposed cassette by means of dedicated hardware linked to the identification station's personal computer. Further details on this procedure as well as on the outlook of the cassette are described in U.S. Pat. No. 4,960,994.

The exposed and identified cassette is then fed into a read out station that is provided with means for reading out the data stored in the EEPROM and for storing these data in a central memory and with means for reading the radiographic image stored in the photostimulable phosphor screen.

The examination type read out of the EEPROM controls selection of corresponding parameters for set up of the read out electronics as well as for the image processing to be performed on the read out image. These parameters were stored in advance in a look up table in the memory of the read but apparatus following a customization procedure as has been described in European patent application 94201183.4 filed Apr. 29, 1994. Next, variable contents of the EEPROM are erased whereas fixed contents are kept or updated.

The image in the screen is read out and subjected to processing taking into account the read-out settings and the processing parameters corresponding with the identified examination type.

The patient identification information is further used in the reproducing apparatus when an identification window is printed on the reproduction of the radiographic image.

Another type of identification system has been disclosed in U.S. Pat. No. 5,264,684 issued Nov. 23, 1993. The disclosed identification system is based on the use of one-dimensional bar codes for identifying the patient, the examination type, and the cassette and on the use of a non-volatile touch memory attached to the cassette to store collected barcodes.

A patient is provided with a unique barcode on a patient chart or alternatively on a bracelet around the wrist.

The examination and exposure conditions are listed on a separate chart as sets of barcodes, of which the applicable ones are scanned by means of a hand-held bar code reader. The hand-held barcode reader is equipped with a memory probe by means of which the barcode keys are transferred to the touch memory provided on the cassette conveying the photostimulable phosphor screen.

In this disclosure identification of various items is performed by means of one-dimensional bar codes. The system is not adequate in case a hospital does not use bar codes for identification of these items.

Further, the disclosed bar codes are one dimensional barcodes. These codes have a limited storage capacity that is adequate for storing a key that refers for example to an address to retrieve information from a look up table or to a file system where more detailed information can be retrieved. Their storage capacity is however not adequate for storage of full identification data.

Identification of an examination type is performed by reading one of a set of bar codes printed on a chart. Such a mode of operation is not flexible. Addition or amendment of an examination type requires that a new chart be produced or at least requires that the chart be adapted.

Bar code charts might get lost and are subject to wear.

Bar codes in general are WORM devices (write once read many) and cannot be used for updating information. The ability to update information is a very attractive feature because it would provide storage of examination specific history information along with patient identification data.

OBJECTS OF THE INVENTION

It is an object of the present invention to provide a system for identification of a radiographic image that is stored in a photostimulable phosphor screen.

It is a further object to provide an identification system that is versatile and can be applied with different patient identification options available in different hospitals.

It is a further object of the invention to provide such a system that enables update of stored data.

Further objects will become apparent from the description hereafter.

STATEMENT OF THE INVENTION

The objects of the present invention are achieved by a photostimulable phosphor radiography identification system comprising identification means for identifying a patient, a cassette for conveying a photostimulable phosphor screen, said cassette being provided with a radiofrequency tag or being provided with means onto which a radiofrequency tag can be attached, a read/write terminal for acquiring data identifying a patient from said identification means and for acquiring data identifying an examination type and for writing said data identifying a patient and said data identifying an examination type onto a radiofrequency tag, a device for reading a radiographic image stored in a photostimulable phosphor screen and for reading data stored by a radiofrequency tag and for processing an image read from a screen in accordance with data read from said radiofrequency tag.

Cassette

According to the present invention a photostimulable phosphor screen is conveyed in a cassette that is provided with a radiofrequency tag (either permanently present on the cassette or attachable to the cassette) wherein data such as patient identification data, data regarding the examination type and data relating to a destination type are stored.

A radiofrequency tag (in the following referred to as RF tag) operates on the basis of data transfer by means of radio frequencies emitted by an RWD antenna connected to e.g. a personal computer or a read/write terminal (often referred to as R/W terminal).

The R/W coil of the RWD generates by magnetic induction a constant field strength that is sufficient to power the tag's circuitry and the memory of the tag and also to generate a system clock on the tag.

RF tags are available in credit card form, in badge form, in self-contained stainless steel can or moulded in plastic for ruggedized design.

As has already been mentioned, in one embodiment the radiofrequency tag onto which the patient identification data and examination type identification data are written by the read/write terminal, is the radiofrequency tag that is provided on the cassette conveying a photostimulable phosphor screen.

In another embodiment these data are written onto a radiofrequency tag that is mountable to and detachable from the cassette. In this case the cassette needs to be provided with means onto which the radiofrequency tag can be attached.

The following is one specific example of such attaching means specifically designed for attachment of two radiofrequency tags.

A mechanical disposition for attaching radiofrequency tags comprises two holes to hold two identical cylindrically shaped RF tags, one of which is fixed in its disposition by screw thread on its jacket (casing), and serves as main data carrier onto which data transmitted by the portable R/W terminal, are written.

The other dual disposition is used to hold an RF tag mounted on a credit card. This rf-tag can easily be placed in position by fast fixing means such as bayonet-catch or alternatively by an affixture of a magnetized card onto a magnetized disposition.

When a specific embodiment of the short cut option is used wherein no read/write terminal is used and wherein patient identification data are directly written onto an Rf tag in credit card form (this short cut option is described in greater detail further on in the description), the main RF tag can be removed to avoid read/write ambiguity, or alternatively it may remain in place provided that the card which holds the second RF tag acts as a magnetic shield to prevent reading/writing the permanent RF tag.

In an alternative disposition, ambiguous identification inherent to inductive operation of the RF technology, is completely avoided by providing the cassette with an RF tag block with one hole only, either holding a screw-thread mounted permanent RF tag or providing space for a slightly smaller RF tag tag fixed on a magnetized card, magnetically attached to the block.

The described attaching means are only exemplary. It is evident that alternative attaching means are possible.

The cassette further is made from lightweight alloy acting as magnetic shield to prevent any unintended read/write of RF tags on other nearby cassettes.

The location of the RF tag or the location of the means for attaching an RF tag to the cassette is preferably the same for all cassettes independent of their format so that when a cassette is fed into the read out device, read out of the information from the tag is always possible.

This can for example be obtained by spacing the location of the RF tag or of the attaching means by a given distance from a predetermined reference point such as the middle line of the cassette.

Means for Identifying a Patient

The means for identifying a patient is in a first embodiment a bar code, preferably a two-dimensional bar code.

Such a two-dimensional bar code identification can for example be produced as follows. The identification data of a patient are entered on a personal computer at the administration desk of a hospital. Then a label, for example a self-adhesive label, can be produced by means of a bar code printer, said label comprising a two-dimensional bar code representation of the identification data of the patient.

If the patient's identification data are already available on some kind of data base system, such as a hospital information system (HIS) or a radiology information system (RIS) it is evident that the identification data need not to be entered once more and that a two-dimensional bar code representation can be produced by forwarding the patient data already available via a network link to a barcode printer connected on the network or connected to a PC or workstation.

In the following, whenever a radiology information system (RIS) is mentioned, it is to be understood that the explanation also holds for a hospital information system (HIS).

More details on two dimensional bar codes and on their storage capacity have been published in IEEE computer magazine, Jun. 1992, page 18, "Information Encoding with Two-Dimensional Bar Codes".

A suitable two-dimensional bar code is the PDF417 code. This code enables coding of approximately 100 characters on a square centimeter, almost 2000 alpha numeric characters can be stored into one symbol, it is easily producible and can be encrypted so that the information is not readable for unauthorized persons and it can be encoded to achieve higher storage efficiency (such as Lempel-Zif-Welch encoding). Printers for producing such bar codes are produced by a number of manufacturers.

The embodiment wherein the identification is performed by printing identification data in the form of a two-dimensional bar code is advantageous because it is cheap and offers the opportunity to fully encode all patient data without the need for a hospital wide computer network.

This embodiment still requires that identification data are entered into the system manually (if no network is available) at some point in time, or retrieved via RIS link to the requesting PC or workstation. However, the identification can be performed at the registration desk of the hospital, a location where identification is part of the job and needs not to be performed at a dedicated identification station in the radiology room where identification is commonly performed by an operator of the exposure unit rather than by a secretary.

The two-dimensional bar code identification constitutes a portable data files and its format is most conveniently the one used in the RIS system to exchange data. An accepted format for exchange of medical data is the ACR-NEMA standard. Preferably this format is adhered to in order to ensure compatibility.

In another embodiment the means for identifying a patient comprise a silicon identification device, such as a touch memory or an RF tag or an EEPROM (electrically erasable programmable read only memory).

The operation of a touch memory is based on data transfer from a read-write probe onto the device by physically contacting the probe and the memory.

Touch memory devices are described in the brochure entitled "Touch The Future" distributed by Dallas Semiconductor, Dallas, Tex. Such a memory device is shown in this brochure that is attached to a patients's hospital identification bracelet and also to a nurse's badge.

It has also been suggested in the above-identified U.S. Pat. No. 5,264,684 to use this type of memory device as an identification device provided on a cassette for conveying a photostimulable phosphor screen.

A radiofrequency tag (also called RF transponder or RF tag) operates on the basis of data transfer in a contactless way from a read-write device to the RF tag as has been described before.

The use of these so-called silicon devices is advantageous in that the devices can be re-written or updated leaving prior data unmodified. This feature can be used to incrementally store all examinations a patient has undergone so that the hospital administration can read out the tag to retrieve the patient's examination history.

The silicon identification devices are re-usable, they can typically be re-written 100,000 times. They are not subject to wear.

Silicon identification devices have a unique manufacturer's identification number so that such a device provided on a cassette uniquely identifies the cassette.

Read/Write Terminal

Read/write terminals as used in the system according to the present invention are available on the market. These devices need to be (1) able to acquire information from at least one form of data carrier carrying patient identification data and (2) able to transfer the acquired data to a radiofrequency tag, more specifically either to a radiofrequency tag provided on the cassette conveying a photostimulable phosphor screen or to a radiofrequency tag that can be attached to the cassette. In the last embodiment the radiofrequency tag is preferably implemented in the form of a credit card.

It is preferred that the device is programmable so that it can run a program displaying a hierarchically organized structure of radiologists' names and examination types selected by a radiologist and so that upon selection of a specific examination type by an operator, this examination type can be written in a file stored in the read/write device. A graphical user interface and/or touch keys provide user-friendly manipulation for this kind of application.

The read/write terminal is customized and configured by means of radiologist specific data files. In these files parameter sets are stored for linking an examination type with parameters for film layout and image processing and with a destination device where the digitized image is sent to upon completion of the digitization process. The customization and configuration software needed to produce these radiologist specific files can run either on the portable read/write terminal itself or on a stand-alone PC, in which latter case the resulting data sets are afterwards downloaded to the portable R/W device via serial communication link. Customization and configuration of a portable read/write device constitutes a refinement of a method for customization and configuration for a digital storage phosphor radiography system disclosed in unpublished European patent application 94201183.4.

It is further advantageous that the R/W device comprises means for displaying a number of destination types to which a read out image (processed or not procesed) can be transmitted, for selecting a specific one of the displayed destination types and for storing a selected destination type. All selectable destinations are known to the R/W terminal after the aforementioned configuration process, and can be either hardware devices such as a film laser printer connected to the digitizer or shared on a computer network, a review console for medical screening and diagnosis, an archival station, or a software copy in the form of a binary file on a disk of local or remote workstation. The given destinations are not exhaustive and comprise any device reachable and supported by current communication technology such as LAN or WAN, digital cellular wireless data transmission link, satellite link, internet link or optical link. The chosen destination type will be written together with patient data, image processing menu, layout settings onto an RF tag on the cassette for subsequent use by the digitizer.

For the ease of manipulation in a hospital environment it is further advantageous that the read/write terminal is a low weight portable device.

The read/write terminal must be able to read data from at least one means for identification of a patient. Preferably however, the device is capable of reading data from a number of data carriers (as enumerated further on).

It is advantageous that the read/write terminal is further capable of exchanging data in a bidirectional and wireless way via RE transmission with a host computer acting as a RIS/HIS server for all portable R/W terminals acting as RIS/HIS clients and currently operated on in the radiology department. This allows inter alia to update the hospital (or radiology information system).

The availability of such wireless site limited link is exemplified hereafter with existing commercially available extension modules for portable computing devices. A wireless RIS link connection offers to the operator the opportunity to retrieve a list of all patients stored in the RIS and have this list displayed on his screen, and further to select one of them in the process of identifying patient with cassette. The bidirectional link further allows to transmit the information on the examination type performed on the patient back to the RIS database.

All patient data thus retrieved from RIS link, plus examination type image processing menu and layout setting, plus destination type are then transmitted by the R/W device onto the RF tag on the cassette.

An operational wireless RIS system thus allows to omit the need for patient identification on any physical data carrier (means for identifying a patient).

The system according to the invention then comprises
- a cassette for conveying a photostimulable phosphor screen, said cassette being provided with a radiofrequency tag or being provided with attaching means onto which a radiofrequency tag can be attached,
- a read/write terminal having means for providing radiofrequency transmission of data to and from a host acting as server in a hospital information system (HIS), means for acquiring data identifying an examination type and for writing acquired data onto a radiofrequency tag,
- a device for reading a radiographic image stored in a photostimulable phosphor screen and for reading data stored by a radiofrequency tag provided on or attached to said cassette and for processing an image read from a screen in accordance with data read from said radiofrequency tag.

An example of suitable read/write device is the PSION HC Dos Handheld Computer (PSION HC is a trademark of the company PSION UK PLC, England). This device comprises a F8680A Chips & Technology processor operating at 7.68 MHz with benchmark performance equivalent to a 8086 @40 MHz running under a DOS operating system on flash EPROM. It comprises internal RAM memory. Different types of this acquisition device exist that have different storage capacity. It further features one or more removable Solid State Disks (SSD) for application programs/data storage and has optional RAM or Flash SSDs. The acquisition device further has a reflecting LCD screen and an alphanumeric keyboard. The device can be programmed off-line on any IBM PC compatible using a cross-compiler, development tools and code download link. The LCD screen allows windowed graphical user interface. The device has internal expansion slots supporting a range of peripherals such as bar-code scanner, RF transponder read/write system, RF data communication link, serial/parallel communications, printer. The apparatus can even be extended by means of two of the above extensions attachable to the upper and lower side of the device. It is powered for autonomous operation by rechargeable batteries, with fast charge available through a cradle system. The apparatus further has communication capabilities with computing systems via an RS 232 port, a modem or a high speed interface. External communication is further possible via a desktop or wall-mounted cradle.

The terminal has a software controlled graphical interface that is user-friendly. Applications can be developed that use different fonts, icons, symbols; even diagrams, maps and illustrations can be displayed.

The use of this type of terminal has been described for several applications such as automatic stock control, automatic entrance control and account debiting. The use of devices of the above named kind for the combination of patient identification and associated examination type identification in a digital radiography environment and more particularly in connection with a digital radiography system wherein a radiographic image of a patient is stored in a photostimulable phosphor screen that is conveyed in a cassette provided with an RF tag or having means for attaching a RF tag, has not been suggested in the prior art disclosures.

Apparatus are available to provide an RF wireless communication link with a host device such as a PSION HC R400/800.

Another example is the PPT portable pen terminal of Symbol Technologies Inc., that has equivalent computing capacity (F8680A processor; 14 MHz clock, 1 Mb Flash: EPROM; 1 Mb RAM Standard) running the DOS operating system and CIC PenDOS for user interface via pen, and featuring a 600×200 pixel CGA resolution reflective LCD display with stylus. Communication facilities are similar through serial RS 232 interface, cradle interface and high performance wireless LAN connection module.

Connectable to any of these programmable portable devices is the bar code laser scanning device PDF 1000 of Symbol Technologies Inc., New York, that allows scanning two-dimensional bar codes, has a single or dual port for serial interfacing via RS 232 link, and allows communication with a wide range of personal computers and terminals. The two dimensional symbology PDE 417, and all major one dimensional symbologies (UPC-E, EAN-8, EAN-13, UPC-A, Code 39 full ASCII, Code 128, Interleaved ⅔, Codabar) can be read.

Read Out Device

A read out device for reading a radiation image stored in a photostimulable phosphor screen in the context of this invention comprises means for reading the information from the RF tag on the cassette (the RF tag being fixed or in a credit card form attachable to the cassette) in addition to means for reading the image stored in the photostimulable phosphor screen.

The means for reading the data stored in the RF tag are a read/write antenna probe and steering electronics.

The physical location of the tag is such that its distance to the front edge of the cassette parallel to the fast scan direction and its distance to the center line parallel to the slow scan direction is fixed for all types of cassettes, such that no mechanical dislocation of the read/write antenna probe is needed with respect to the cassette independent of its physical dimensions.

On entry of the cassette in the feeder of the read-out apparatus, the cassette is moved in the so-called slow scan direction, and at the time of passing the antenna probe, the tag is read out synchronously. An aperture of suitable size in the slow scan cassette carriage allows read/write access with a fixed mount antenna (approx. diameter 10 cm) lying in a plane parallel to the cassette's plane. The antenna power is adjusted to yield reliable reading/writing of the RF tag, giving the fixed perpendicular distance of the antenna plane to the cassette plane. Said perpendicular distance does not exceed typically 10 cm, and falls well inside the R/W range of commercially available antenna steering electronics.

The amount of time needed to read/write the tag is proportional to the storage capacity of the tag, but does not exceed 1 sec. for commercially available tags.

The slow scan time period typically lasts 50 sec. such that only a fraction of it is simultaneously occupied by reading/writing the tag. The feeder cabinet is further provided with electromagnetic shielding to avoids any unwanted interference with neighbouring cassette tags in the feeder.

The means for reading the radiographic image stored in the photostimulable phosphor screen comprise means for generating a beam of stimulating light of the appropriate wavelength such as a laser, means for deflecting the stimulation light onto the screen such as a galvanometer or a polygon mirror, means for detecting light emitted by the screen upon stimulation for converting detected light into a digital signal representation of the image for example a photomultiplier and an analog-to-digital convertor.

The read out device further comprises means for storing the signal representation of the radiographic image as well as the adjustment parameters for the components of the read out device (for example photomultiplier voltage) and image processing parameters that are associated with certain examination types.

The read out device still further comprises means for processing the signal representation of an image taking into account processing parameters associated with an examination type read out from the RF tag on the cassette and read out from the above memory.

Identification Procedure

The identification, read out and processing procedure is summarized as follows:

- first a patient is identified by writing his identification data onto identification means (EEPROM, touch memory, RF tag, bar code or communication link to radiology information system (RIS) or hospital information system (HIS)),
- then the identification data are read by means of a read/write device from said identification means and they are stored,
- by means of the read/write device an examination type is selected and data relating to the selected examination type are stored in the read/write device,
- the patient identification data and the examination type identification data are written onto a RF tag already provided on a cassette conveying a photostimulable phosphor screen or on a RF tag attachable to such a cassette (the screen either having been exposed or going to be exposed to X-rays),
- after exposure, tie cassette conveying the photostimulable phosphor screen is fed into a read out device where the RF tag is read out and the image on the screen is read.

In a specific embodiment a destination type is also indicated, selected and stored by means of the read/write terminal and written onto the RF tag on the cassette.

Read out of the image is performed by the read out device having its components (e.g. photomultiplier voltage) adjusted in accordance with adjustment parameters corresponding with the examination type read from the RF tag.

Processing of the image read out from the exposed screen is performed using processing parameters that correspond with the examination type read out from the RF tag.

Finally the processed image is displayed on a monitor or applied to a hard copy recorder for producing a visible enhanced radiographic image. Density values created in the hard or soft copy image are controlled by the values of the processed image signal representation.

Transmission of the processed image to the display device or the hard copy recorder or any other destination is in one embodiment indicated by destination type data written on the RF tag.

In an alternative short cut embodiment of the present invention no read/write terminal is provided.

The patient's identification data are written onto a RF tag preferably in credit card format (also called smart card) that is then adhered to a cassette conveying a photostimulable phosphor screen.

Following exposure to X-rays, the cassette is entered in a read out apparatus wherein both the information in the smart card and the image stored in the photostimulable phosphor screen are read. Next the signal representation of the radiographic image is processed and the processed image is displayed or reproduced as a hard copy image.

Two conditions make this short cut possible:

1) either the smart card is issued by a department performing a standard examination type, thus requiring a default setting of the processing and read out conditions. In this situation, the examination type can be encoded in the smart card in advance. Such cards can be discriminated from other cards by the colour or by a label etc. The smart card thus serves as an electronic label or tag requiring minimal operator handling. This modality is particularly advantageous for specialized departments such as mammography, radiotherapy, orthopaedics . . .

2) the examination type is automatically determined from an evaluation of the image content by means of an image processing algorithm, thus making input of examination type data superfluous.

It would also be possible to write other data onto the RF tag such as examination type data, or data identifying a destination type.

In still another embodiment, a read/write terminal provided with a wireless RIS link is used. A wireless RIS link provides on-line access to a database of all patients currently registered in the hospital. A list of patient names is then retrieved at connect time and displayed on the screen of the read/write device, after which a selection is made, or by default, the last patient chosen is assumed to be the next.

In this mode of operation no patient identification means are required. The remainder of the operation is identical to that described higher.

The RIS link operates bi-directionally. This means that the examination type selected on the read/write terminal and other relevant information with regard to the examination (date, radiologist name, department, film type . . . ) can be updated in the RIS database.

The hardware responsible for a wireless digital link between the (handheld) read/write terminal and the RIS server is offered by an extension module on the portable, in direct communication with a transceiver on the network to which the RIS server is connected.

A cost-effective alternative to a wireless RIS link is offered by current technology known as cradle. Here the handheld read/write terminal is by intervals put in a cradle, being connected in a small network of cradles interconnected by hardwired serial link (RS 232 . . . 485 or standard low cost 2 wires cable e.i. telephone cable) and the RIS server. During a sequence of identifications, all RIS related information is stored temporarily on the local hard disk of the computing device. On deposit of the handheld read/write terminal in the cradle, the data is transferred instantaneously to the RIS server and updates the RIS database.

The hardwired link with the RIS database is preferred in situations in which a wireless link is difficult to implement, particularly in hazardous environment (e.g. electromagnetic interference of NMR apparatus) or when a 100 % sustained network operation is mandatory.

BRIEF DESCRIPTION OF THE DRAWINGS

Particular aspects of the present invention as well as preferred embodiments thereof will be explained by means of the corresponding drawings wherein.

DETAILED DESCRIPTION

Figure 1:
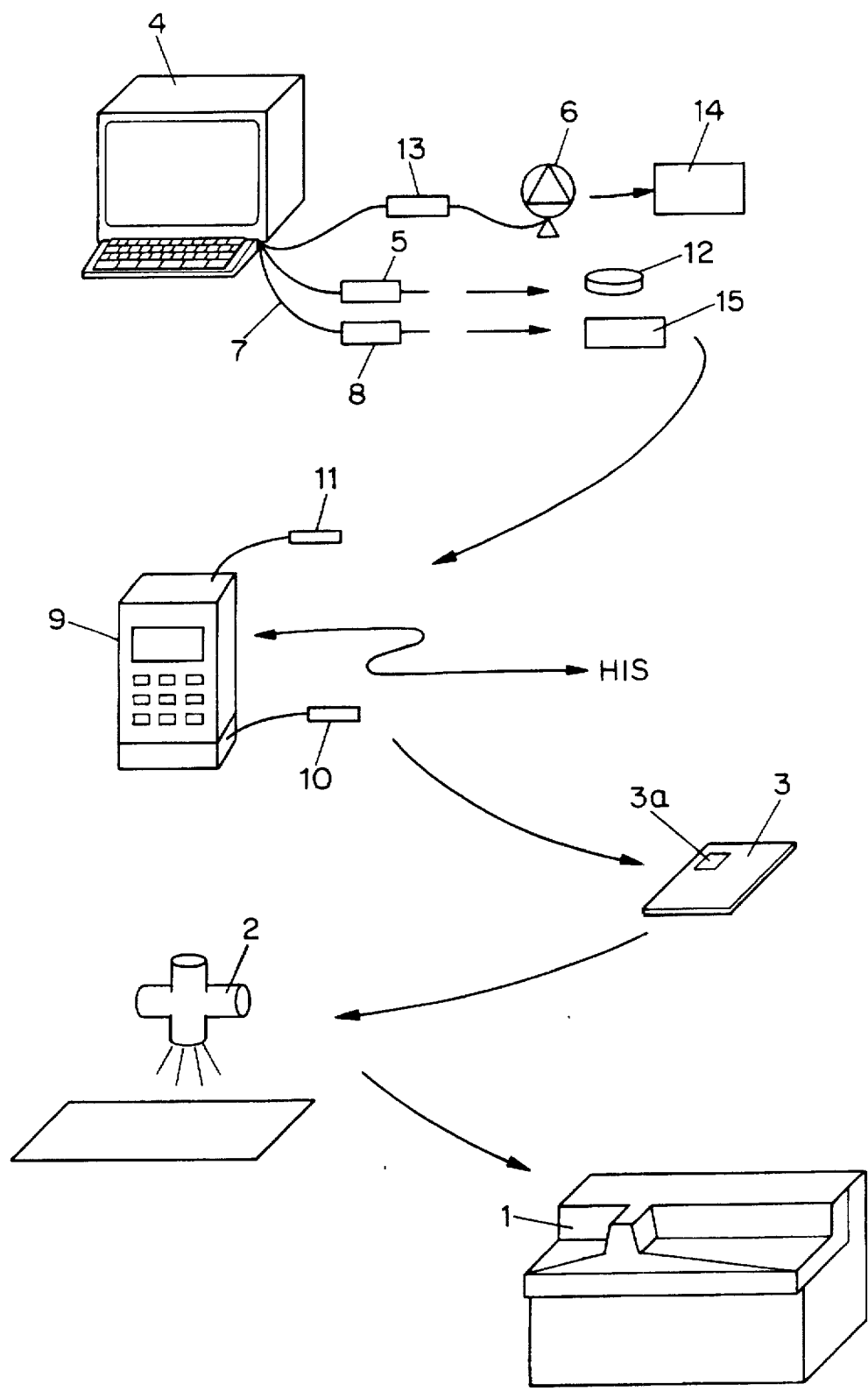
FIG. 1 is a general view of a system in which the method of the present invention can be applied.

A simplified diagram of a system in which the present invention can be implemented, is shown in FIG. 1.

At the time of entry of a patient at the hospital's administration desk an identifying badge was produced for the patient.

For this purpose patient identification data such as the patient's name, date of birth etc. were entered into a personal computer (4) or a workstation (not shown).

For patients visiting the hospital for the first time, the identification data were entered manually; for patients already known in the hospital's data base, the data were retrieved in this database.

The personal computer (or workstation) was provided with a touch probe (5) enabling data transfer from said personal computer to a touch memory (12).

In an alternative embodiment, it was provided with a probe (6) and corresponding steering electronics (13) for transferring data to an RF tag (14).

Alternatively the hospital can opt for encoding the patient's identification data as a two-dimensional bar code label (15). For this purpose the personal computer would have been provided with a link (7) to a bar code printer (8).

Either of these identification means (touch memory, RF tag, bar code label) can be adhered to a hospital bracelet or to an identification card.

In this specific case patient identification data were transferred to a touch memory device. This touch memory device was attached to a hospital bracelet.

In an alternative embodiment the patient's identification data were encoded in a two-dimensional bar code format as explained below.

The available identification data were first written in a file having a specific format. Then, by a conversion and printing process a two-dimensional bar code was created.

Figure 3:
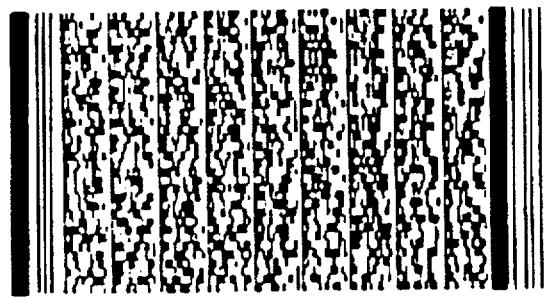
FIG. 3 is an example of two-dimensional bar code label wherein patient identification data are encoded.

The file format consists of three fields for every datum, each being separated by a comma, and terminated by a return character (ASCII 13 '/n'). The first of the fields indicates the ACR-NEMA group number hexadecimal (cfr. column with header 'gr' in the table shown below), the second field indicates the ACR-NEMA element number hexadecimal (cfr. column with header 'el' in the table shown below). The third field contains the actual data, in a standard ASCII string (crf. column with header 'field' in the table shown below). If fields are omitted from the two-dimensional bar code, the operator of the identification terminal may add them. Also, when some fields require modification at the time of identification, the operator may modify these fields after the code has been read. example of a two-dimensional bar code is shown in FIG. 3.

An example height is 30 mils, the module width is 10 mils, the spect ratio is 0.5.

The following fields are supported:

| gr | el | field | num char. | possibilities/ format | example |
|---|---|---|---|---|---|
| 0010 | 0010 | patient name | 33 char | | (Smith) |
| 0010 | 1001 | patient other names | 20 char | | (Helen) |
| 0010 | 0020 | patient code | 15 char | | (007) |
| 0010 | 0040 | patient sex | 1 char | (M/F/O) | (F) |
| 0010 | 0030 | patient birthday | 8 char | YYYYMMDD | (19761002) |
| 0019 | 4000 | exam type | 20 char | | (thorax) |
| 0019 | 4001 | exam sub type | 20 char | | (general) |
| 0019 | 1262 | exposure class | 20 char | 25 50 100 . . . 800 | (400) |
| 0008 | 1060 | radiologist | 20 char | | (Prof. Johnson) |
| 0020 | 0020 | patient orientation | 20 char | (AP/PA/OTHERS) | (AP) |
| 0021 | 0040 | cassette orientation | 20 char | (horizontal/ vertical) | (vertical) |
| 0020 | 4000 | comment | 33 char | | (this is comment) |
| 0000 | 5170 | number of copies | 1 char | (1 . . . 9) | (2) |
| 0010 | 4000 | info field | 12 char | | (user info) |
| 0020 | 0010 | ris id | 16 char | | (007) |
| 0001 | 5173 | hardcopy destination | 20 char | | (ADC_LR1) |
| 0001 | 5172 | processing dest. | 20 char | | (ADC_PS1) |
| 0001 | 5171 | archive destination | 20 char | | (ADC_AS1) |
| 0001 | 5174 | review destination | 20 char | | (ADC_RS1) |

In the radiology room first the patient's identification data were read by a portable read/write terminal (9) of the type PSION HC provided with a probe (10) for reading touch memories. These identification data were stored in a file in the read/write device.

Next, a program was run on the read/write terminal displaying a list of radiologists names. The name of the radiologist ordering examination of the patient was selected by the operator. Upon selection of the radiologist's name a list of examination types were displayed, all of them relating to the medical specialisation field of the selected radiologist. From this list the specific examination that was to be performed was selected and transferred to the same file where the patient's identification data were stored in the read/write device.

Next, these data (patient identification and the examination type identification linked thereto) were transferred via an RF probe (11) of the read/write terminal (9) onto a radiofrequency tag (3a) provided on a cassette conveying a photostimulable phosphor screen.

Then, the patient was exposed to x-rays (2) and the x-ray image was stored in a photostimulable phosphor screen (3) conveyed by the identified cassette provided with a radiofrequency tag (3a).

The exposed cassette was then entered in a radiation image read-out apparatus (1) where the information stored in the RF tag and the image stored in the photostimulable phosphor screen were read-out.

A probe in the read out device positioned on a location where it was in a position to read the RF tags on each of the cassettes independently of their format, transferred the information stored in the RF tag on the cassette to the internal memory of the read out device.

Figure 2:
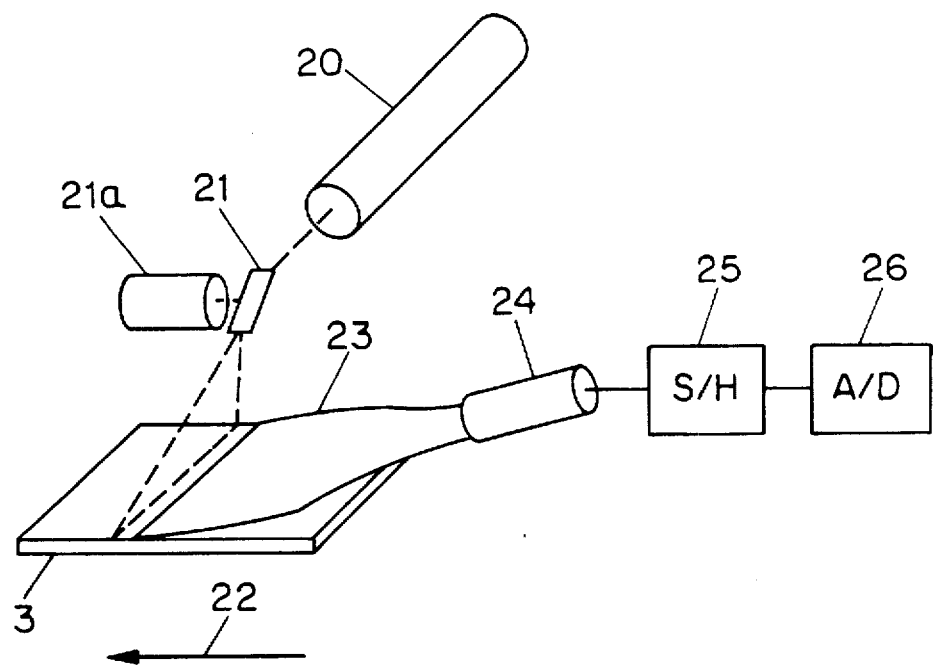
FIG. 2 is a detailed view of a system for reading an image stored in a photostimulable phosphor screen.

The stored image was read-out by scanning the phosphor screen with stimulating rays as shown in FIG. 2. Stimulating rays were emitted by laser (20), emitting light of a wavelength adapted to the stimulation spectrum of the phosphor used.

The stimulating rays were deflected into the main scanning direction by means of galvanometric deflection means (21, 21a). The subscanning was performed by transporting the phosphor screen in the subscanning direction indicated by arrow (22). The stimulated emission was directed by means of a light collector (23) onto a photomultiplier (24) for conversion into an electrical image representation.

Next, the signal was sampled by a sample and hold circuit (25), and converted into a digital raw image signal by means of an analog to digital convertor (26).

The digital image signal was sent to the image processing module of the read-out apparatus where it was stored in an internal buffer.

The signal representation of the radiographic image was then processed taking into account the parameters corresponding with the identified examination type and the processed image was displayed or applied to an output recorder for production of a hard copy.

On completion of read out the variable data on the RF tag can be erased. Also the residual image left on the read out photostimulable phosphor screen is erased so that the screen-cassette assembly is ready to be re-used.

Although the invention has been described with reference to specific embodiments, it will be understood that variations and modifications can be effected without departing from the spirit and scope of the present invention.

I claim:

1. A photostimulable phosphor radiography identification system comprising identification means for identifying a patient,
   a cassette for conveying a photostimulable phosphor screen, said cassette being provided with a cassette radiofrequency tag,
   a hand-held read/write terminal arranged for acquiring data identifying a patient from said identification means and for acquiring data identifying an examination type and for writing said data identifying a patient and said data identifying an examination type onto said radiofrequency tag, and provided with means for reading information from a plurality of identification means of different types,
   a device for reading a radiographic image stored in a photostimulable phosphor screen and for reading data stored by said radiofrequency tag and for processing an image read from a screen in accordance with data read from said radiofrequency tag.

2. A system according to claim 1 wherein said identification means is a two-dimensional bar code label.

3. A system according to claim 1 wherein said identification means is a patient radiofrequency tag.

4. A system according to claim 3 wherein said cassette radiofrequency tag is attachable to attaching means on said cassette.

5. A system according to claim 1 wherein said identification means is a touch memory device.

6. A system according to claim 1 wherein said identification means is an EEPROM.

7. A system according to claim 1 wherein said read/write terminal is programmable.

8. A system according to claim 7 wherein said read/write terminal further comprises means for displaying a plurality of examination types, means for selecting an examination type and associating it with said patient identifying data, and means for storing said selected examination type.

9. A system according to claim 7 wherein said read/write terminal further comprises means for displaying destination data representing a plurality of destinations, means for selecting at least one of the destinations identified by said destination data and associating said selected destination with said patient identifying data, and means for storing data representing said selected destination.

10. A system according to claim 7 wherein said read/write terminal comprises a graphical user interface.

11. A system according to claim 1 wherein said device for reading a radiographic image comprises means for scanning said screen with stimulating radiation, means for detecting light emitted by said screen upon stimulation, and means for converting said detected light into a signal representation.

12. A photostimulable phosphor radiography identification system comprising a cassette for conveying a photostimulable phosphor screen, said cassette being provided with a memory,
   a read/write terminal having means for providing radiofrequency transmission of data to and from a host acting as server in a hospital information system (HIS), means for acquiring data identifying an examination type and for writing said acquired data onto said memory,
   a device for reading a radiographic image stored in a photostimulable phosphor screen and for reading data stored by said memory and for processing an image read from a screen in accordance with data read from said memory.

13. A system according to claim 12 wherein said read/write terminal is programmable.

14. A system according to claim 12 wherein said read/write terminal further comprises means for displaying a plurality of examination types, means for selecting an examination type and associating it with patient identification data, and means for storing said selected examination type on said memory.

15. A system according to claim 12 wherein said read/write terminal further comprises means for displaying destination data representing a plurality of destinations, means for selecting at least one of the destinations identified by said destination data and associating said selected destination with patient identification data, and means for storing data representing said selected destination on said memory.

16. A system according to claim 12 wherein said read/write terminal comprises a graphical user interface.

17. A system according to claim 12 wherein said device for reading a radiographic image further comprises means for scanning said screen with stimulating radiation, means for detecting light emitted by said screen upon stimulation, and means for converting said detected light into a signal representation.

18. A system according to claim 12 wherein said memory is a radiofrequency tag.

19. A system according to claim 12 wherein said read/write terminal is hand-held.

20. An identification method for use in a photostimulable phosphor radiography system comprising the steps of identifying a patient by writing the patient's identification data onto identification means,
   reading said identification data from said identification means by means of a hand-held read/write terminal and storing said identification data,
   displaying on said hand-held read/write terminal a plurality of examination types,
   selecting on said hand-held read/write terminal one of the displayed examination types and associating the selected examination type with said identification data and storing the examination type, writing said identification data and said examination type onto a radiofrequency tag provided on a cassette conveying a photostimulable phosphor screen, exposing said cassette to x-rays so as to store an x-ray image in the screen, providing said cassette to a read out device, reading the identification data and the examination type stored in said radiofrequency tag, and reading the X-ray image stored in said screen, processing the X-ray image read out of the screen in accordance with the data identifying an examination type.

21. An identification method according to claim 20 comprising the further steps of displaying on said read/write terminal destination data representing a plurality of destinations, selecting on said read/write terminal at least one of the destinations identified by said destination data, associating said selected destination with said identification data, and storing data representing said selected destination, writing data representing said selected destination onto said radiofrequency tag, reading said data representing said selected destination from said radiofrequency tag when said cassette is provided to the read out device.

22. A method according to claim 20 wherein said step of reading said X-ray image comprises scanning said screen with stimulating radiation, detecting light emitted upon stimulation, and converting said detected light into a signal representation.

23. An identification method for use in a photostimulable phosphor radiography system comprising the steps of identifying a patient by writing the patient's identification data onto a radiofrequency tag, adhering said radiofrequency tag onto a cassette conveying a photostimulable phosphor screen, exposing said screen to x-rays so as to store an x-ray image in the screen, providing said cassette to a read out device, reading the identification data stored in said radiofrequency tag, and reading the X-ray image stored in said screen.

24. A method according to claim 23 comprising the further steps of writing data representing a destination onto said radiofrequency tag, reading said data representing said destination from said read out device, and transmitting said image to said destination.

25. A method according to claim 23 wherein said step of reading said X-ray image comprises scanning said screen with stimulating radiation, detecting light emitted upon stimulation, and converting said detected light into a signal representation.

26. An identification method for use in a photostimulable phosphor radiography system comprising the steps of identifying a patient by retrieving by means of a read/write terminal at least patient identification data from a hospital information system through radiofrequency transmission of data from a host device acting as server for said hospital information system, writing said patient identification data by means of said read/write terminal onto a memory provided on a cassette conveying a photostimulable phosphor screen, exposing said cassette to x-rays so as to store an x-ray image in the screen, providing said cassette to a read out device, reading the identification data stored in said memory, and reading the X-ray image stored in said screen.

27. A method according to claim 26 comprising the further steps of displaying on said read/write terminal a plurality of examination types, selecting on said read/write terminal one of the displayed examination types, associating it with said identification data, and storing it, writing a selected examination type onto said memory, reading the selected examination type from said memory in the read out device and processing the X-ray image read out of the screen in accordance with said examination type.

28. A method according to claim 26 comprising the further steps of displaying on said read/write terminal destination data representing a plurality of destinations, selecting on said read/write terminal at least one of the destinations identified by said destination data, associating said selected destination with said identification data, and storing data representing said selected destination, writing data representing said selected destination onto said memory, reading said data representing said selected destination from said memory in the read out device and transmitting the X-ray image after processing to a destination identified by said data representing said selected destination.

29. A method according to claim 26 wherein said hospital information system is updated through radiofrequency transmission of data from said read/write terminal to said host device.

30. A method according to claim 26 wherein said step of reading said X-ray image comprises scanning said screen with stimulating radiation, detecting light emitted upon stimulation, and converting said detected light into a signal representation.

31. A system according to claim 26 wherein said read/write terminal is hand-held.

32. A system according to claim 26 wherein said memory is a radiofrequency tag.

33. A photostimulable phosphor radiography identification system comprising identification means for identifying a patient, a cassette for conveying a photostimulable phosphor screen, said cassette being provided with a radiofrequency tag, a read/write terminal arranged for acquiring data identifying a patient from said identification means and for acquiring data identifying an examination type and for writing said data identifying a patient and said data identifying an examination type onto said radiofrequency tag, a device for reading a radiographic image stored in said photostimulable phosphor screen and for reading data stored by said radiofrequency tag and for processing an image read from a screen in accordance with data read from said radiofrequency tag.

* * * * *

UNITED STATES PATENT AND TRADEMARK OFFICE
CERTIFICATE OF CORRECTION

PATENT NO. : 5,757,021
DATED : May 26, 1998
INVENTOR(S) : Piet Dewaele

It is certified that error appears in the above-indentified patent and that said Letters Patent is hereby corrected as shown below:

Column 2, line 23, "read but" should read --read out--;

Column 4, line 13 "rf-tag" should read --RF tag--;

Column 4, line 19, "Rf tag" should read --RF tag--;

Column 4, line 31, "tag tag fixed" should read -- tag fixed --;

Column 4, line 35, "as magnetic" should read -- as a magnetic --;

Column 5, line 28, "data files" should read -- data file, --;

Column 5, line 43, "patients's" should read -- patient's --;

Column 6, line 35, "procesed" should read -- processed --;

Column 8, line 1, "digital:" should read -- digital --;

Column 8, lines 12 and 13, "Flash: EPROM;" should read -- Flash EPROM, --;

UNITED STATES PATENT AND TRADEMARK OFFICE
CERTIFICATE OF CORRECTION

PATENT NO. : 5,757,021
DATED : May 26, 1998
INVENTOR(S) : Piet Dewaele

It is certified that error appears in the above-indentified patent and that said Letters Patent is hereby corrected as shown below:

Column 8, line 25, "PDE" should read -- PDF --;

Column 8, line 64, "avoids" should read -- avoid --;

Column 9, line 40, "tie" should read -- the --;

Column 11, lines 63 and 64, "example of a . . . shown in Fig. 3" should be deleted;

Column 11, line 66, "An example height" should read -- An example of a two-dimensional bar code is shown in figure 3, the module height--.

Column 11, line 67, "spect ratio" should read -- symbol aspect ratio --;

Column 12, line 40, "radiologists" should read -- radiologists' --

Signed and Sealed this

Twelfth Day of October, 1999

Q. TODD DICKINSON

*Attesting Officer*   *Acting Commissioner of Patents and Trademarks*